United States Patent
Újvári

(10) Patent No.: US 8,929,678 B2
(45) Date of Patent: Jan. 6, 2015

(54) METHOD FOR AUTOMATIC CONTOUR FILTER POSITIONING FOR MEDICAL X-RAY IMAGING

(75) Inventor: Tamás Újvári, Torchheim (DE)

(73) Assignee: General Electric Company, Schenectady, NY (US)

( * ) Notice: Subject to any disclaimer, the term of this patent is extended or adjusted under 35 U.S.C. 154(b) by 308 days.

(21) Appl. No.: 13/601,751

(22) Filed: Aug. 31, 2012

(65) Prior Publication Data

US 2013/0051526 A1 Feb. 28, 2013

(30) Foreign Application Priority Data

Aug. 31, 2011 (EP) .................................. 11462013

(51) Int. Cl.
*A61B 6/06* (2006.01)
*A61B 6/00* (2006.01)

(52) U.S. Cl.
CPC ................ *A61B 6/06* (2013.01); *A61B 6/4035* (2013.01); *A61B 6/5217* (2013.01); *A61B 6/542* (2013.01)
USPC ........... 382/266; 382/132; 382/268; 382/272; 382/274; 382/286; 378/51; 378/54; 378/56; 378/62

(58) Field of Classification Search
USPC ................. 382/132, 266, 268, 272, 274, 286; 378/51, 54, 56, 62
See application file for complete search history.

(56) References Cited

U.S. PATENT DOCUMENTS

| | | | |
|---|---|---|---|
| 4,125,776 A | 11/1978 | Tosswill | |
| 5,270,549 A | 12/1993 | Engdahl | |
| 5,447,617 A | 9/1995 | Shieh | |
| 5,559,853 A | 9/1996 | Linders | |
| 5,602,891 A * | 2/1997 | Pearlman | 378/62 |
| 5,625,665 A | 4/1997 | Fokkink | |
| 5,666,396 A * | 9/1997 | Linders et al. | 378/156 |
| 5,732,121 A * | 3/1998 | Takeo et al. | 378/62 |
| 5,751,786 A | 5/1998 | Welters | |
| 5,754,618 A * | 5/1998 | Okamoto et al. | 378/4 |
| 5,832,055 A * | 11/1998 | Dewaele | 378/62 |
| 5,901,240 A * | 5/1999 | Luo et al. | 382/132 |
| 6,108,403 A * | 8/2000 | Cooper et al. | 378/156 |
| 6,118,855 A | 9/2000 | Welters | |
| 6,370,228 B1 * | 4/2002 | Mockler et al. | 378/158 |
| 6,584,173 B2 | 6/2003 | Zwart | |
| 6,587,598 B1 * | 7/2003 | Devillers et al. | 382/284 |
| 6,708,055 B2 * | 3/2004 | Geiser et al. | 600/425 |
| 6,891,967 B2 * | 5/2005 | Prince | 382/150 |
| 6,920,238 B1 * | 7/2005 | Chen et al. | 382/128 |
| 7,260,170 B2 * | 8/2007 | Arenson et al. | 378/4 |
| 7,292,721 B2 * | 11/2007 | Arnold | 382/131 |
| 7,376,254 B2 * | 5/2008 | Barth | 382/131 |
| 7,391,848 B2 * | 6/2008 | Spahn | 378/98 |
| 7,519,207 B2 * | 4/2009 | Luo et al. | 382/128 |

(Continued)

*Primary Examiner* — David A Vanore
(74) *Attorney, Agent, or Firm* — GE Global Patent Operation; Marc A. Vivenzio

(57) ABSTRACT

A method is provided for automatic contour filter positioning for medical X-ray imaging in an X-ray apparatus comprising a collimator and at least one movable contour filter actuated by a motor based positioning subsystem, wherein a digital image in a frame of rows and columns of pixels is rendered for processing and obtaining control data for applying a contour filter. The method comprises identifying exposure of subareas, preparing for filter positioning, and defining filter position.

17 Claims, 3 Drawing Sheets

(56) References Cited

U.S. PATENT DOCUMENTS

| | | | |
|---|---|---|---|
| 7,545,979 B2* | 6/2009 | Fidrich et al. | 382/173 |
| 7,593,555 B2* | 9/2009 | Spahn | 382/128 |
| 7,697,743 B2* | 4/2010 | Metz | 382/131 |
| 7,711,169 B2* | 5/2010 | West et al. | 382/128 |
| 7,792,339 B2* | 9/2010 | Li | 382/128 |
| 7,903,861 B2* | 3/2011 | Luo et al. | 382/132 |
| 7,916,912 B2* | 3/2011 | Abramov et al. | 382/128 |
| 7,923,801 B2* | 4/2011 | Tian et al. | 257/440 |
| 7,941,000 B2* | 5/2011 | Rongen et al. | 382/294 |
| 8,050,509 B2* | 11/2011 | Jeong et al. | 382/261 |
| 8,094,896 B2* | 1/2012 | Dutta et al. | 382/128 |
| 8,238,637 B2* | 8/2012 | Ratner et al. | 382/132 |
| 8,416,916 B2* | 4/2013 | Schutz | 378/62 |
| 8,594,410 B2* | 11/2013 | Schmidt et al. | 382/132 |
| 8,774,485 B2* | 7/2014 | Blaskovics et al. | 382/132 |
| 2003/0153823 A1* | 8/2003 | Geiser et al. | 600/407 |
| 2006/0023842 A1 | 2/2006 | Sohal | |
| 2006/0110068 A1* | 5/2006 | Luo et al. | 382/289 |
| 2013/0230222 A1* | 9/2013 | Wang et al. | 382/131 |
| 2013/0343630 A1* | 12/2013 | Moulik | 382/131 |

\* cited by examiner

METHOD FOR AUTOMATIC CONTOUR FILTER POSITIONING FOR MEDICAL X-RAY IMAGING

FIELD OF THE INVENTION

Embodiments of the present invention relate generally to a method for automatic contour filter positioning for medical X-ray imaging.

BACKGROUND OF THE INVENTION

Medical X-ray imaging is quite sensitive to the attenuation of X-rays by the actual human object examined The dynamic range of the images often comprises overexposed and/or underexposed parts where no details can be recognized.

U.S. Pat. No. 5,625,665 discloses an X-ray apparatus provided with a filter for limiting the dynamic range of an X-ray image formed on an X-ray detector. The filter has filter elements including one or more capillary tubes, one end of which communicates with a reservoir with an X-ray absorbing liquid. The adhesion of the X-ray absorbing liquid to the inner side of the capillary tubes can be adjusted by means of an electric voltage applied to an electrically conductive layer provided on the inner side of the capillary tubes. The degree of filling of the capillary tubes with the X-ray absorbing liquid is adjusted by way of the electric voltage value. The X-ray absorption profile can be adjusted within a short period of time, for example within one second, by adjustment of the electric voltages applied to the capillary tubes. This is a versatile filter, but adapting it to an existing X-ray apparatus is expensive.

Some X-ray apparatuses comprise so called contour filters used for changing dynamic range locally and also decreasing X-ray load. These are shaped metallic sheets, different ones of which may come in a set. A selected one of the sheets is pushed in place to provide a given attenuation of the passing through X-rays. Positioning of contour filters is traditionally carried out by manual control of the user. This manual positioning is, however, is often not effective.

Due to the disadvantages of the prior art methods, especially manual positioning the contour filters, there is a need for providing a method which makes it possible to improve the quality and dynamic properties of X-ray medical images where a set of contour filters is available. There is also a need for automated selection and positioning of a contour filter without any change in the relevant contour filter unit of the X-ray apparatus.

BRIEF DESCRIPTION OF THE INVENTION

Embodiments of the invention relate to a method for automatic contour filter positioning for medical X-ray imaging in an X-ray apparatus comprising a collimator and at least one movable contour filter actuated by a motor based positioning subsystem, wherein a digital image in a frame of rows and columns of pixels is rendered for processing, and wherein control data is obtained for applying a contour filter. The method comprises identifying exposure of subareas, which comprises the sub-steps of: segmenting the image into subareas; computing a local EPT (equivalent patient thickness) for each subarea as average brightness of the pixels included in the subarea; computing an overall average of the local EPTs; and providing an EPT difference map by subtracting the overall average of the local EPTs from each local EPT. The method further comprises preparing for filter positioning, which comprises the sub-steps of: adding a single pixel wide border to the EPT-difference map by assigning one border pixel to each row and column, and computing the pixel values of the border as a weighted average of all the pixels in the corresponding row or column, the weighting factor being proportional with the distance between the pixel and the corresponding border pixel. The method further comprises defining filter position, by identifying two groups of negative value border pixels starting from the lowest values, on two different sides of the image, where the ends of the filter position will be located.

BRIEF DESCRIPTION OF THE DRAWINGS

The invention will now be described in detail with reference to the accompanying drawings, in which.

DETAILED DESCRIPTION OF THE INVENTION

Figure 1:
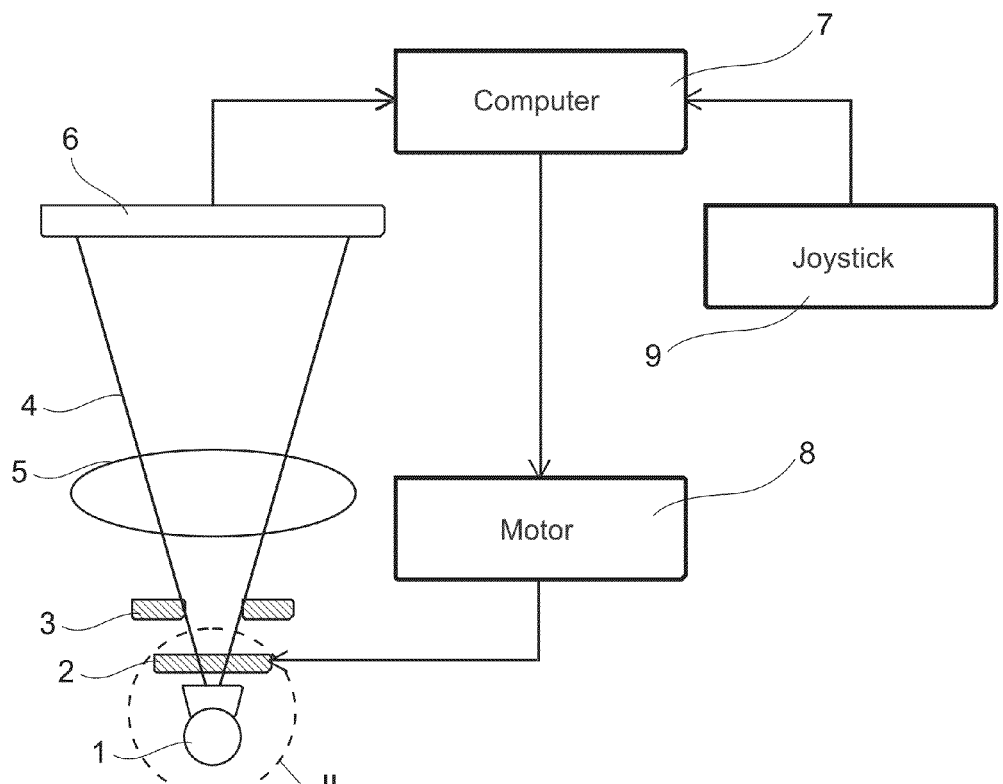
FIG. 1 is a simplified schematic structure of a medical X-ray imaging apparatus.

FIG. 1 illustrates a simplified schematic exemplary structure of a medical X-ray imaging apparatus comprising an X-ray tube 1, a next contour filter 2, and a collimator 3. The X-ray tube 1 generates a quite disperse X-ray radiation, which is formed to a sharp beam 4 by the collimator 3. This can be carried out by movable blades or in other embodiments an iris. The corresponding obtained aperture of beam 4 is rectangular or round. The contour filter 2 can be arranged between the X-ray tube 1 and the collimator 3, near to the latter. The contour filter and the collimator 3 can be mounted into a common unit.

After penetrating through the body of a patient 5 the beam 4 reaches a detector 6 which transform the projected X-ray image into a visible image. The X-ray apparatus comprises a computer 7 among others for processing the image frames from the detector 6. A set of movable contour filters 2 but at least one is driven by a motor 8 which is provided to actuate the selected contour filter 2. A joystick 9 is connected to the computer 7 to manually position a contour filter 2. In line with the object of the invention, however, an automatic control for positioning a proper contour filter 2 is provided by the method implemented by the computer 7 and the motor 8.

Figure 2:
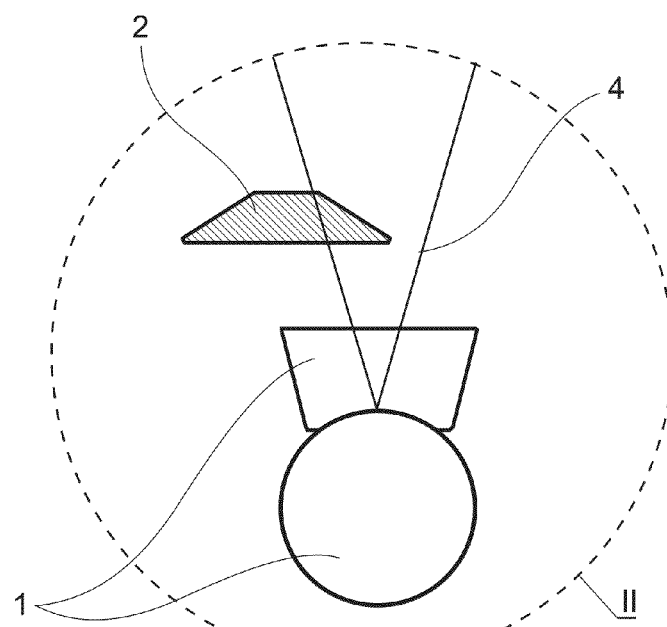
FIG. 2 is an enlarged part II of FIG. 1 with a specific contour filter.

FIG. 2 shows an enlarged part II of FIG. 1. A specific contour filter 2 has been placed in a partially crossing way into the beam 4. The contour filter 2 has a trapezoid cross-section which provides a linearly growing attenuation at its edge. The contour filter 2 is typically made of a metal sheet with versatile contour outline form. A selected contour filter 2 is pushed in the beam 4 from outside of the collimated aperture. Its principal role is to improve image quality and to reduce the X-ray dose to both the patient, and the medical staff Medical X-ray imaging frequently uses techniques in which a sequence of fairly similar exposures is taken or a continuous X-ray monitoring is applied. In these cases a first image frame is accessible and the present method makes it possible to select and position automatically a contour filter to this specific image frame. When the subsequent images are taken, if the image frames have a little change in their content, that position is most likely optimal also to enhancing those as well.

The first image is an image frame of x,y coordinate direction rows and columns of pixels. It is rendered for processing by a method and thus obtaining control data for applying a contour filter 2.

EPT (equivalent patient thickness) is used as a metric of the X-ray attenuation of an object (or patient). It has been defined as the thickness of a PMMA (plexi-glas) block that has the same x-ray attenuation as the measured object in a given x-ray spectrum.

Figure 3:
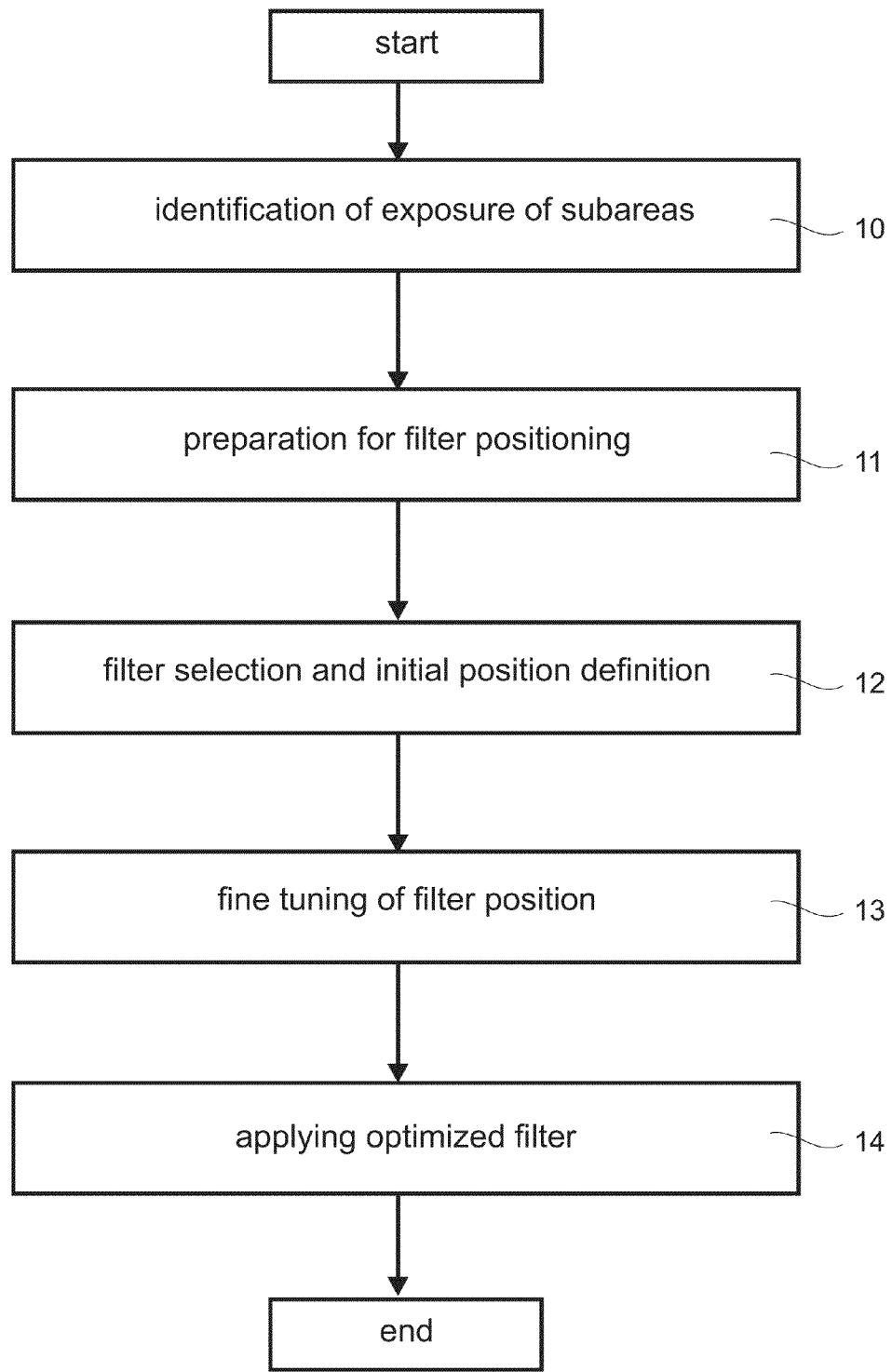
FIG. 3 is a schematic flowchart diagram of a method according to an embodiment of the invention.

The method, in an embodiment illustrated in FIG. 3, may comprise identifying overexposed areas. The first image frame is segmented into smaller subareas, for example, rectangular subareas, including m pixels in x direction and n pixels in y direction. Here m and n are positive integer numbers. The subareas can be squares, when m=n, but it is not necessary. The size of the subareas in an embodiment is $2 \leq m \leq 100$ and $2 \leq n \leq 100$, but in another embodiment $5 \leq m \leq 30$ and $5 \leq n \leq 30$. Local EPT (equivalent patient thickness) is then computed for each subarea as the average brightness of the pixels included in the subarea. An overall average of the local EPTs is computed, an EPT-difference map is provided by subtracting the overall average of the local EPTs from each local EPT, and subareas of negative values are defined as being overexposed, and the positive values are defined as being underexposed.

The method may further comprise preparing for filter positioning, which comprises adding a single pixel wide border to the EPT-difference map by assigning one border pixel to each row and column. The pixel values of the border are computed as a weighted average of all the pixels in the corresponding row or column. The weighting factor is proportional with the distance between the pixel and the corresponding border pixel. The weighting factor, in an embodiment, is linearly proportional with the distance between the pixel and the corresponding border pixel. Thus the border is determined substantially by the region toward the close edge of the EPT-difference map. Then a decision is made whether introducing a given contour filter 2 is sensible or not. Sensible means here that image quality improvement can be reached by placing the given contour filter in. It is the case if there are overexposed areas that are significantly brighter than the average.

The method may further comprise selecting a filter and defining an initial position. Two groups of negative value border pixels are identified starting from the lowest values. Any known region growing method can be useful for this purpose. The initial position of the contour filter 2 will be by the ends of these groups. The optimal filter width and thickness is selected based on the shape, and the maximum EPT value of the EPT-difference map pixels falling under a contour filter 2. The contour filter EPT is maximized by selecting a contour filter from the set of at least one contour filter provided, while avoiding underexposed areas, and the smallest, which is big enough to cover the area. Alternatively, all negative border pixels can be segmented into groups, and the first contour filter 2 can be placed over the biggest group, or the decision can be made based on a complex metric based on group size and negativeness.

The method may further comprise fine tuning of filter position, which comprises trying each combination of forward/backward steps along the border pixels, and checking the EPT distribution of the EPT-difference map pixels covered by the selected contour filter 2. The final position of the contour filter 2 is determined by metrics to assess a goodness of a position based on the criteria to avoid both over, and underexposed pixels in the image. Random perturbations of decreasing magnitude are added to the filter position, and select or reject the new positions based on the position goodness metrics. The optimized filter position is defined on the basis of best goodness metrics.

The method may further comprise applying an optimized filter position, which comprises actuating the selected contour filter 2 at the optimized contour filter position by moving it with a motor 8. The optimized contour filter position can be applied automatically or after an approval stage offered to the user. The approval stage offered to the user in an embodiment comprises accepting and modifying options. The approval stage may comprise a manual modifying option, for example, by the joystick 9 of FIG. 1.

Figure 4:
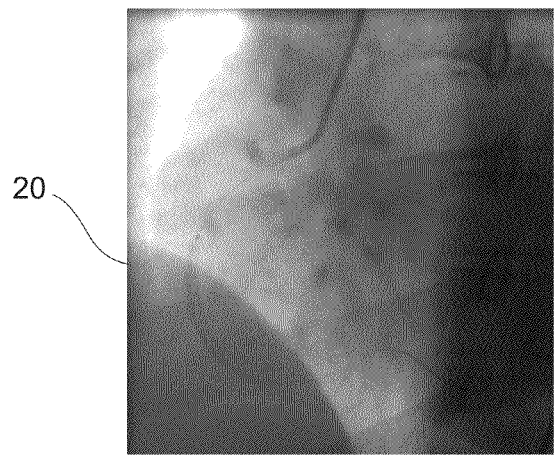
FIG. 4 is an X-ray image frame.
Figure 5:
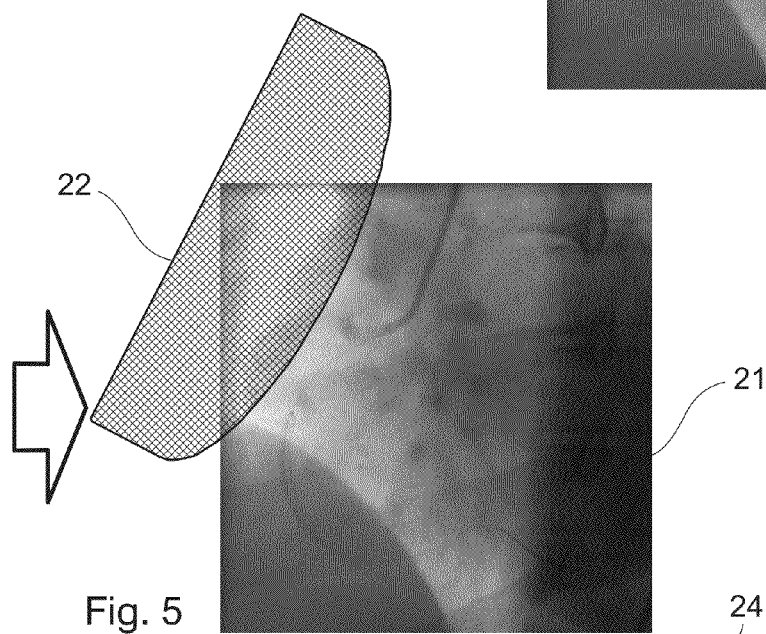
FIG. 5 is the X-ray image frame of FIG. 4 with an applied contour filter.
Figure 6:
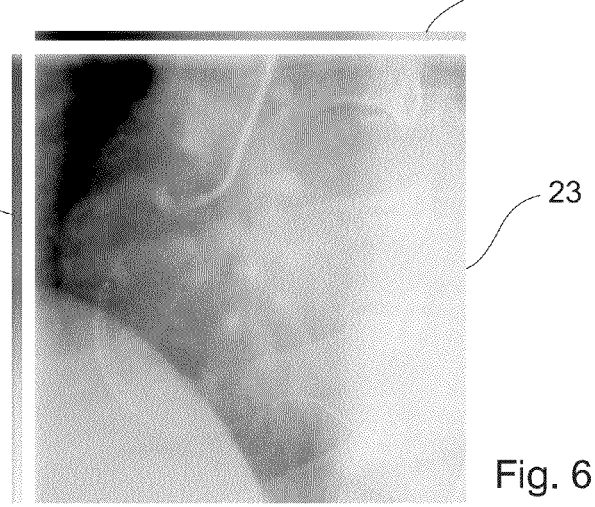
FIG. 6 is an EPT-difference map derived from the image frame of FIG. 4, with border pixels on the left and top sides.

FIG. 4 shows a medical X-ray image 20 as for example. The upper left part of the image 20 can be considered overexposed. This part can be attenuated by using a contour filter 22 as shown in FIG. 5. The resulted image 21 will show more details in the upper left part where the contour filter 22 is applied. FIG. 6 shows two borders 24, 25 added to the EPT-difference map 23 computed from the pixels of image 20. The weighting factor was linearly proportional with the distance between the pixel and the corresponding border pixel. Thus, the border pixels of border 24 are determined by the top region of the EPT-difference map, while the border pixels of border 25 are determined by the left region of the EPT-difference map.

In another embodiment, a method comprises identifying exposure of subareas, preparing for filter positioning, and defining a filter position. The exposure of subareas is identified at least in part by: segmenting an image into subareas, the image comprising a frame of rows and columns of pixels that is rendered for processing in an X-ray apparatus comprising a collimator and at least one movable contour filter actuated by a motor based positioning subsystem; computing respective local EPTs for the subareas, wherein for each subarea the local EPT of the subarea is computed based on an average brightness of the pixels included in the subarea; computing an overall average of the local EPTs; and providing an EPT-difference map by subtracting the overall average of the local EPTs from each local EPT. The step of preparing for filter positioning comprises: adding a single pixel wide border to the EPT-difference map by assigning one border pixel to each row and column; and computing the pixel values of the border as a weighted average of all the pixels in the corresponding row or column, the weighting factor being proportional with the distance between the pixel and the corresponding border pixel. The step of defining the filter position comprises identifying two groups of negative value border pixels starting from the lowest values, on two different sides of the image, where the ends of the filter position will be located.

The advantage of the methods described above is the possible elimination of the time consuming contour filter selection and positioning, while reserving the option of modification by the user.

The proposed method for automatic contour filter positioning makes it possible to improve X-ray image quality without efforts of the user, especially in cases of images which contain overexposed or underexposed subareas.

Due to this improvement, health care professionals can obtain more reliable information from consecutive similar images, for example, for further diagnostic or therapeutic actions. At the same time, in most of the cases, this will not require human efforts other than accepting it as being an automated method.

What is claimed is:

1. A method for automatic contour filter positioning for medical X-ray imaging in an X-ray apparatus comprising a collimator and at least one movable contour filter actuated by a motor based positioning subsystem, wherein a digital image in a frame of rows and columns of pixels is rendered for processing, the method comprising:
   identifying exposure of subareas, comprising:
      segmenting the image into subareas;
      computing a local EPT for each subarea as average brightness of the pixels included in the subarea;
      computing an overall average of the local EPTs; and
      providing an EPT-difference map by subtracting the overall average of the local EPTs from each local EPT;
   preparing for filter positioning, comprising:
      adding a single pixel wide border to the EPT-difference map by assigning one border pixel to each row and column; and
      computing the pixel values of the border as a weighted average of all the pixels in the corresponding row or column, the weighting factor being proportional with the distance between the pixel and the corresponding border pixel; and
   defining filter position, comprising:
      identifying two groups of negative value border pixels starting from the lowest values, on two different sides of the image, where the ends of the filter position will be located.

2. The method of claim 1, wherein identifying exposure of subareas further comprises:
   defining subareas of negative values as overexposed, and subareas of positive values as underexposed in the EPT-difference map.

3. The method of claim 2 further comprising fine tuning the filter position, comprising:
   trying each combination of forward/backward steps along the border pixels, and checking the EPT distribution of the EPT-difference map pixels covered by the contour filter;
   determining a final filter position of the contour filter by metrics to assess a goodness of a position based on criteria of avoiding both overexposed pixels and underexposed pixels in the image;
   adding random perturbations of decreasing magnitude to the filter position, and selecting or rejecting the new positions based on the position goodness metrics; and
   defining filter position on the basis of best goodness metrics.

4. The method of claim 2, wherein defining filter position further comprises selecting a filter, comprising:
   selecting an optimal filter width and thickness based on the shape, and the maximum EPT value, of the EPT-difference map pixels falling under a contour filter; and
   maximizing the contour filter EPT by selecting a contour filter from the set of at least one contour filter provided, while avoiding underexposed areas, and selecting the smallest contour filter which is big enough to cover the area.

5. The method of claim 1, wherein preparing for filter positioning further comprises making a decision of whether introducing the contour filter is sensible or not.

6. The method of claim 1, wherein defining filter position comprises identifying a group of negative value border pixels starting from the lowest value using a region growing method.

7. The method of claim 1 further comprising:
   applying the contour filter at the defined filter position.

8. The method of claim 7, wherein applying the contour filter at the defined filter position comprises automatically applying the optimized contour filter position.

9. The method of claim 7, wherein applying the contour filter at the defined filter position comprises applying the optimized contour filter position after an approval stage offered to a user.

10. The method of claim 9, wherein the approval stage offered to the user comprises accepting and modifying options.

11. The method of claim 10, wherein the approval stage offered to the user comprises a manual modifying option.

12. The method of claim 1, wherein the subareas are rectangular including m×n pixels, wherein m and n are positive integer numbers.

13. The method of claim 12, wherein $2 \leq m \leq 100$ and $2 \leq n \leq 100$.

14. The method of claim 12, wherein $5 \leq m \leq 30$ and $5 \leq n \leq 30$.

15. The method of claim 1, wherein the weighting factor is inversely linearly proportional with the distance between the pixel and the corresponding border pixel.

16. A method comprising:
   identifying exposure of subareas, comprising:
      segmenting an image into subareas, the image comprising a frame of rows and columns of pixels that is rendered for processing in an X-ray apparatus comprising a collimator and at least one movable contour filter actuated by a motor based positioning subsystem;
      computing respective local EPTs for the subareas, wherein for each subarea the local EPT of the subarea is computed based on an average brightness of the pixels included in the subarea;
      computing an overall average of the local EPTs; and
      providing an EPT-difference map by subtracting the overall average of the local EPTs from each local EPT;
   preparing for filter positioning, comprising:
      adding a single pixel wide border to the EPT-difference map by assigning one border pixel to each row and column; and
      computing the pixel values of the border as a weighted average of all the pixels in the corresponding row or column, the weighting factor being proportional with the distance between the pixel and the corresponding border pixel; and
   defining a filter position, comprising:
      identifying two groups of negative value border pixels starting from the lowest values, on two different sides of the image, where the ends of the filter position will be located.

17. The method of claim 16, further comprising:
   applying one of the at least one movable contour filter at the filter position.

* * * * *

UNITED STATES PATENT AND TRADEMARK OFFICE
CERTIFICATE OF CORRECTION

| | | |
|---|---|---|
| PATENT NO. | : 8,929,678 B2 | Page 1 of 1 |
| APPLICATION NO. | : 13/601751 | |
| DATED | : January 6, 2015 | |
| INVENTOR(S) | : Újvári | |

It is certified that error appears in the above-identified patent and that said Letters Patent is hereby corrected as shown below:

Specification

In Column 1, Line 14, delete "examined" and insert -- examined. --, therefor.

In Column 2, Line 61, delete "staff" and insert -- staff. --, therefor.

Signed and Sealed this
Tenth Day of November, 2015

Michelle K. Lee
*Director of the United States Patent and Trademark Office*